US012766023B1

(12) United States Patent
Roessiger et al.

(10) Patent No.: US 12,766,023 B1
(45) Date of Patent: Oct. 20, 2026

(54) THERAPEUTIC CUSHIONING BOOT WITH STATIC AIR BLADDER

(71) Applicant: EHOB, Inc., Indianapolis, IN (US)

(72) Inventors: Heike Roessiger, Indianapolis, IN (US); Jared Cohen, Indianapolis, IN (US); Christopher Perkins, Carmel, IN (US); Gregory Konkle, Indianapolis, IN (US); Christian Gastaldo, Cleveland, OH (US)

(73) Assignee: EHOB, Inc., Indianapolis, IN (US)

( * ) Notice: Subject to any disclaimer, the term of this patent is extended or adjusted under 35 U.S.C. 154(b) by 0 days.

(21) Appl. No.: 19/258,076

(22) Filed: Jul. 2, 2025

(51) Int. Cl.
*A61F 5/01* (2006.01)
*A61F 13/06* (2006.01)

(52) U.S. Cl.
CPC ............ *A61F 5/012* (2013.01); *A61F 5/0111* (2013.01); *A61F 13/067* (2013.01); *A61F 13/069* (2013.01)

(58) Field of Classification Search
CPC .......... A61F 5/01; A61F 5/012; A61F 5/0111; A61F 5/05816; A61F 5/05833; A61F 5/058; A61F 5/055; A61F 5/34; A61F 13/06; A61F 13/067; A61F 13/069; A61F 13/085; A61H 9/0078; A61H 9/0071; A61H 9/0082; A61H 1/008
USPC .............................................. 602/2, 13, 62
See application file for complete search history.

(56) References Cited

U.S. PATENT DOCUMENTS

| | | | | |
|---|---|---|---|---|
| 9,301,866 | B2 | 4/2016 | Spahn et al. | |
| 10,350,102 | B2 | 7/2019 | Spahn et al. | |
| 10,806,633 | B2 | 10/2020 | Spahn et al. | |
| 11,779,493 | B2 | 10/2023 | Spahn et al. | |
| 2021/0015681 | A1* | 1/2021 | Spahn | A61F 5/30 |
| 2021/0275386 | A1* | 9/2021 | Ravikumar | A61F 5/34 |

* cited by examiner

*Primary Examiner* — Daniel A Miller
(74) *Attorney, Agent, or Firm* — Maginot, Moore & Beck, LLP

(57) ABSTRACT

A therapeutic cushioning boot includes a partially fiber-filled body that defines an interior pocket to removably receive an inflated static air bladder. The body includes a pair of inflation ports configured for the passage of tubing associated with an auxiliary device used with the boot. The boot includes an Achilles bladder, positioned to support the Achilles tendon, that is attached to the static air bladder to define a pair of notches that engage the inflation ports to effectively anchor the air bladder within the interior pocket. The static air bladder is configured to provide an increasing inflated height from the top of the boot toward the foot portion.

10 Claims, 9 Drawing Sheets

THERAPEUTIC CUSHIONING BOOT WITH STATIC AIR BLADDER

BACKGROUND

The present invention relates generally to the field of inflatable devices for supporting the human body, and more particularly is concerned with a novel improved inflatable cushion boot to counter the force amplifications experienced by the foot, and particularly the heel area of the foot, when the body is in, the supine position.

In the supine position, the foot assumes the shape of a wedge that tapers from the toes down to the heel. The mechanical force amplifications that are typically associated with a wedge are therefore also experienced by the wedge-shaped foot. The heel area, and more specifically the points of contact between the heel area and the patient support surface or substrate upon which the body is lying in the supine position, experiences mechanical force amplifications that are analogous to those experienced by the working edge of the typical wedge. In addition, when in the supine position, the lower legs function as levers with the heel areas serving as fulcrums, further amplifying the mechanical forces acting upon the heel areas.

The recognition that heel ulcers are caused by such mechanical forces (pressure, shear and frictional stresses) on the heel became clinically significant in the early 1980's. Since that time it has been found that offloading mechanical forces on the heel is the ideal way to prevent a pressure ulcer of the heel from developing. The first attempt to offload these mechanical forces was to simply rest the leg on pillows to offload the forces on the heel. However, the occurrence of pressure ulcers of the heel continued to increase. The frequency of pressure ulcers of the heel are now similar to that of sacral pressure ulcers.

An inflatable cushioning boot, such as the foot cushion disclosed in U.S. Pat. No. 5,328,445, which issued on Jul. 12, 1994, significantly improved the prevention and treatment of pressure ulcers of the heel and other types of foot wounds. The objectives of the inflatable chambers of the foot cushion of the '445 Patent that defined the foot resting chamber were the offloading of mechanical forces on the heel, providing symmetrical static air support to the calf, ankle and foot, and supporting the sole of the foot to prevent foot drop and resultant injury. This original inflatable foot cushion has been improved since its inception in 1994, such as by the inclusion of a foot gate presented in U.S. Pat. No. 9,301,866, which issued on Apr. 5, 2016. Foot gates allow the caregiver to visually confirm that the heel is offloaded during use, further ensuring patient safety and prevention of pressure injuries. New heel protectors or cushioning boots have been developed that replaced the inflatable chambers with a fiber filling, such as disclosed in U.S. Pat. No. 10,806,633, which issued on Oct. 20, 2020.

SUMMARY OF THE DISCLOSURE

A therapeutic compression boot is provided that comprises an outer panel and an inner panel, each having a common outer perimeter that defines, in a planar open configuration of the boot, a back panel, a first sidewall panel and a second sidewall panel. Each sidewall panel extends from one end of the back panel parallel to each other and separated from each other by a notch. The boot further includes a foot gate including a first overlapping panel that is foldably attached to an end of the first sidewall panel, and a second overlapping panel that is foldably attached to the second sidewall panel. In one feature, the outer perimeter of the outer panel is sewn or welded to the inner panel to define an interior pocket therebetween with an opening at an opposite end of the back panel. The opening and interior pocket are sized and configured to removably receive a static air bladder. The static air bladder includes a sealed outer perimeter defining a first region conforming to and receivable within the first sidewall panel, a second region conforming to and receivable within the second sidewall panel and a third region conforming to and receivable within the back panel. The three regions are in communication and commonly inflated. The inner panel of the boot includes a closure extending beyond the outer panel at the opposite end of the back panel. The closure is configured to be folded over the opening, and the closure and the outer panel including mating fastener strips for releasably fastening the closure to the outer panel to enclose the static air bladder within the interior pocket. At least the inner panel contains a cushioning material in at least a portion of the back panel and in the first and second overlapping panels so that the cushioning of the two panels combines with the inflated air bladder to comfortably support a patient's lower leg and foot while eliminating the risk of pressure ulcers.

In another feature, the boot includes an inflated Achilles bladder separate from the first, second and third regions of the static air bladder. The Achilles bladder is disposed between and connected to the first and second regions adjacent to the notch in the body of the boot to support the lower leg at the Achilles tendon. The outer and inner panels each define a tubing port in each of said first and second sidewall panels that is configured for passage of tubing therethrough associated with auxiliary devices, such as a wound therapy device, that is used inside the therapeutic boot. In particular, the outer and inner panels are connected to each other at or around each tubing port. The Achilles bladder is connected to the first and second regions of the static air bladder to define a pair of notches aligned with and configured to engage each tubing port to retain the static air bladder within the interior pocket.

In a further feature, the static air bladder includes segments having different inflated heights. In particular, the inflated height of the bladder increases from the opening to the interior pocket toward the Achilles bladder. The different inflated heights are created by transverse seams across the middle third of the bladder, with the seams spaced apart by different dimensions to produce the different inflated heights. The therapeutic boot disclosed herein includes a foot strap and a pair of leg straps that are used to span the patient's foot and leg and connect opposite sides of the boot when it is folded about the patient's foot and leg. In one feature, the foot strap is arranged to extend around the boot in one direction, while the two leg straps extend around the boot in the opposite direction.

DETAILED DESCRIPTION

Figure 1:
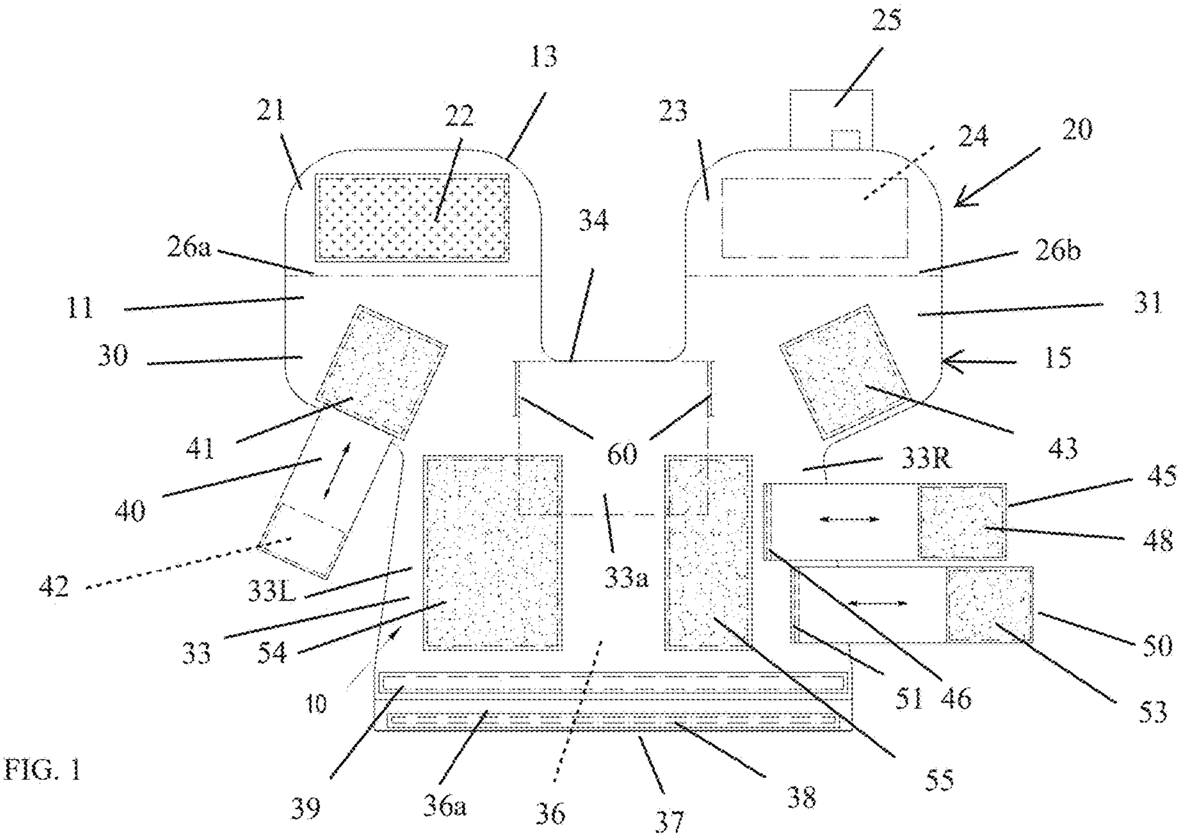
FIG. 1 is a plan view of the exterior face of a therapeutic cushioning boot according to one embodiment in which the boot is shown in its open configuration for receiving the leg and foot of a patient.

For the purpose of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

Figure 2:
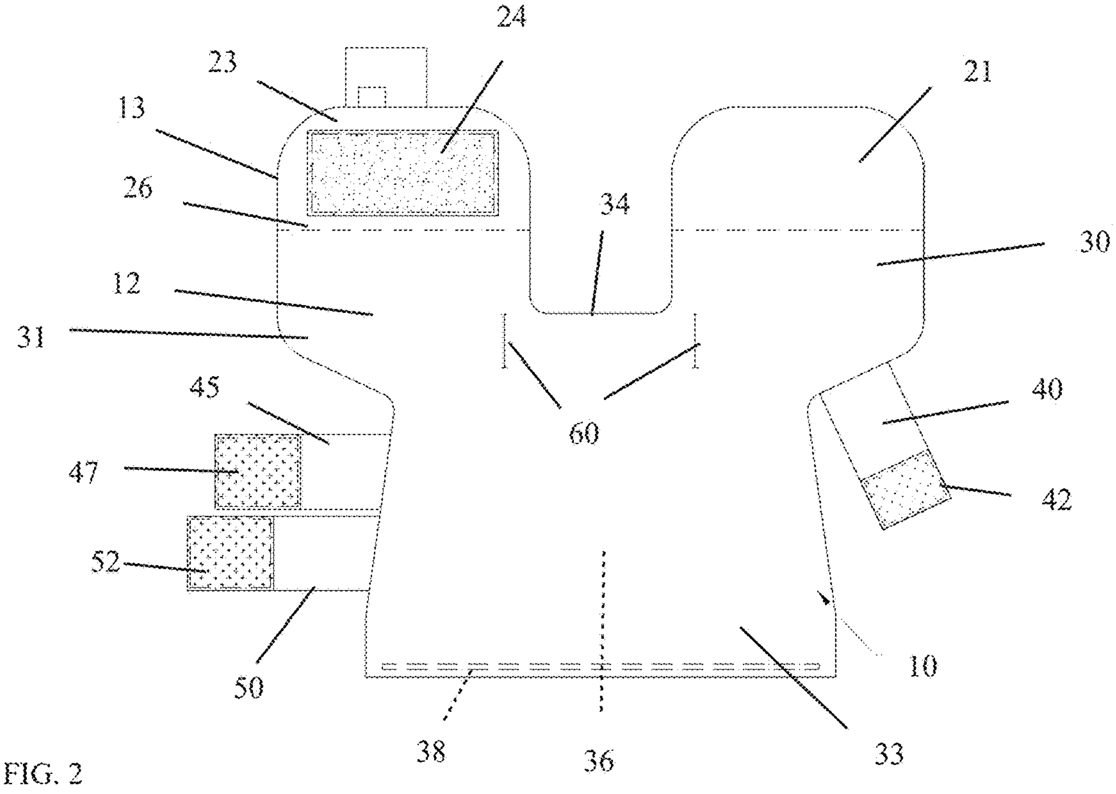
FIG. 2 is a plan view of the opposite interior face the therapeutic cushioning boot shown in FIG. 1.

As shown in FIGS. 1-2, a therapeutic cushioning boot 10 is provided that has an initial open planar configuration. The boot is formed by an outer panel 11 and inner panel 12 that share a common outer periphery and are sewn or welded together around a peripheral seam 13. The panels define an interior pocket 36 therebetween that is configured to receive a replaceable static air bladder 70 (FIG. 3), as described in more detail herein. The periphery of the boot forms a body portion 15 having a first sidewall panel 30, a second sidewall panel 31 and a rear panel 33 that are configured to surround the foot and lower leg of a patient when the boot 10 is folded into its closed configuration (shown in FIGS. 8-14). In particular, the sidewall panels 30, 31 are arranged to flank the patient's foot when the sidewall panels are folded toward each other. The back panel 33 is sized and configured to encircle the back and sides of the lower leg.

The side panels 30, 31 include respective overlapping panels 21, 23 that form a foot gate 20 when the boot 10 is folded into its closed configuration. The first overlapping panel 21 includes a first hook and loop fastener 22 and is separated from the remainder of the side panel 30 by a fold seam 26*a*. The second overlapping panel 23 includes a second hook and loop fastener 24 is separated from the remainder of the side panel 31 by a fold seam 26*b*. The second overlapping panel can include a boot tag 25 that includes printed details of the cushioning boot and its use. In the closed configuration, the two panels 30, 31 are placed in overlapping relation, with the fasteners 22, 24 facing and releasably engaged to each other. Thus, the first overlapping panel 30 is inside the second overlapping panel 31. The foot gate 20 of the therapeutic cushioning boot 10 can be constructed and operated in the manner described in U.S. Pat. No. 10,806,633 (the '633 Patent), the disclosure of which is incorporated herein by reference.

Figure 13:
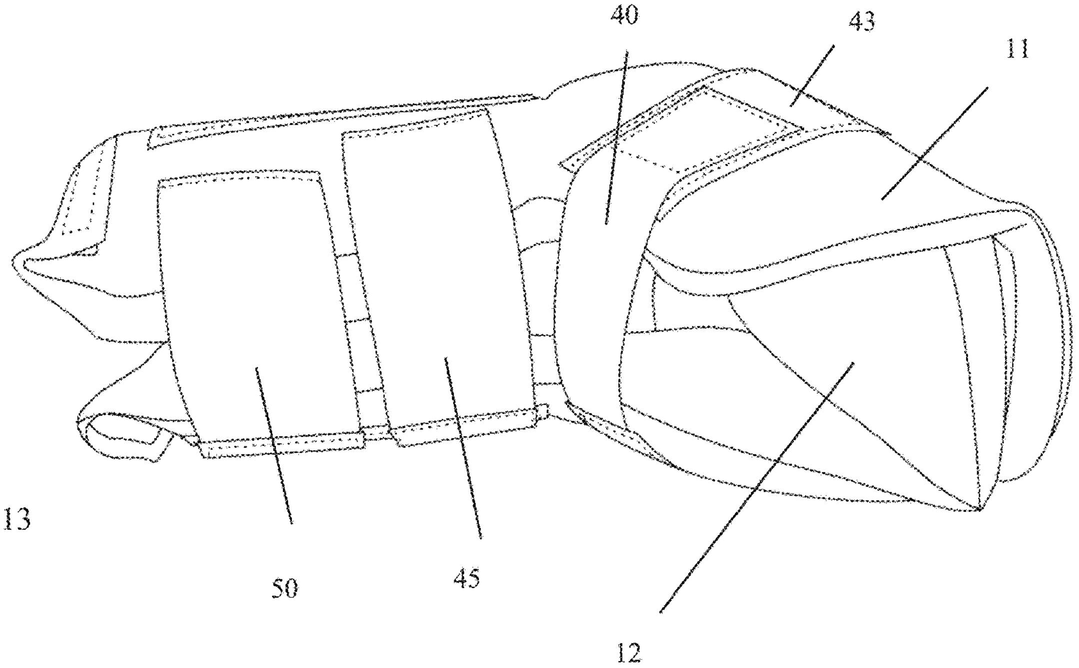
FIG. 13 is a front perspective view of the assembled therapeutic cushioning boot shown in FIG. 8.
Figure 14:
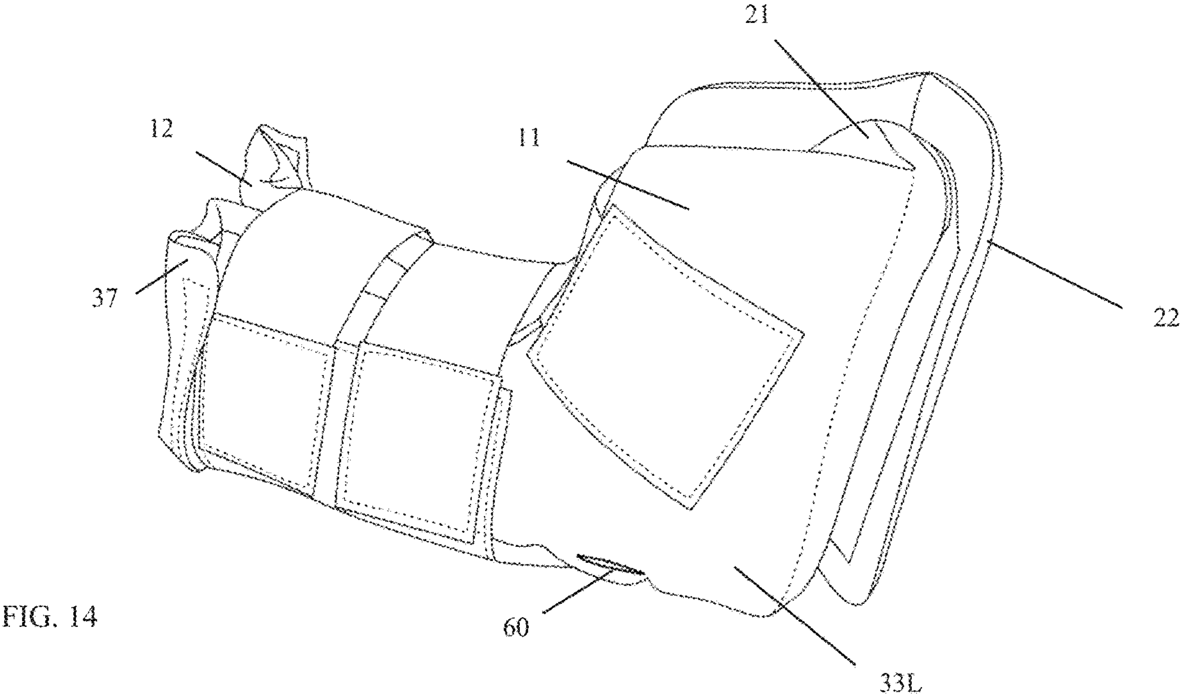
FIG. 14 is a bottom perspective view of the assembled therapeutic cushioning boot shown in FIG. 8.

In one aspect of the boot 10, each of the panels 11, 12 is formed of overlapping sheets sewn together, and at least the outer panel 11 contains a cushioning material 90 (FIG. 4), such as a polyester fiberfill, in certain regions of the boot. In this respect, the panels of the boot 10 can be constructed in a manner similar to that described in the '633 Patent in which the cushioning material is provided in certain densities within the panels. The fiberfill material 90 is provided not only for comfort of the patient but also for firm support of the patient's foot in an upright position. However, the fiberfill 90 is not packed as fully into the panels as in the boot shown in the '633 Patent because the cushioning boot 10 of the present disclosure incorporates a static air cushion, as described in more detail herein. In one embodiment, the cushioning material fills each panel 11, 12 sufficiently to permit a tight, but comfortable fit, around the lower leg to hold the therapeutic boot 10 in position to support the lower leg. As best seen in FIG. 13, less cushioning material is packed into the panels at the sides of the patient's foot to avoid discomfort and to allow a small amount of movement of the foot relative to the lower leg. In another embodiment, the cushioning material is limited to the overlapping panels 21, 23 of the foot gate 20, and to the Achilles region 33*a* of the back panel 33, as shown in the dashed lines in FIG. 1.

In one embodiment, the sheets forming the outer panel 11 are a high-strength, water-resistant material. In specific embodiments, the outer panel sheets are a non-woven material, such as nylon. The sheets forming the inner panel 12 can be a softer material adapted for comfortable support of the patient's foot and leg. In specific embodiments, the inner panel sheets are formed of a micro-fiber or a microsuede.

Figure 4:
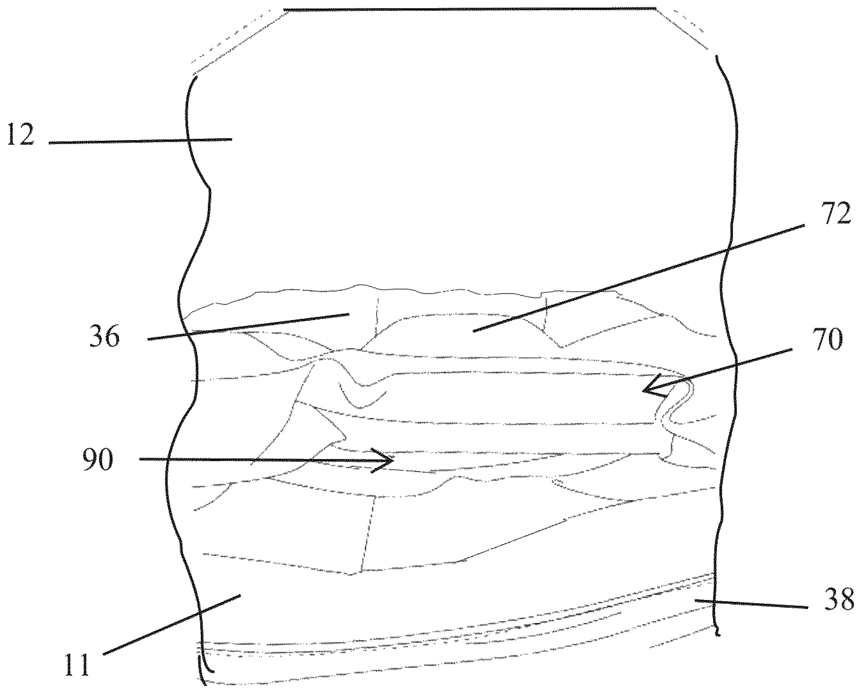
FIG. 4 is an end perspective view of an open end of the therapeutic cushioning boot of FIG. 1 shown with the air bladder of FIG. 3 in position within the boot.

As noted, the inner and outer panels cooperate to form a pocket 36 between the panels. The pocket is configured to receive the static air bladder 70 through pocket opening 36*a*. The opening includes a closure 37 that can be a pair of hook and loop strips 38, 39, with the strip 38 folded over the opening 36*a* to engage the other strip 39 to close the air bladder within the pocket. The static air bladder 70 combines with the fiberfill 90 of the panels 11, 12 to provide an optimum cushioning and pressure redistribution to reduce localized pressure points, particularly on the lower leg, as shown in FIG. 4. This combination of features offers the softness of the fiber-filled panels with the adaptive support of the static air bladder. In turn, this reduces the need for frequent repositioning of the patient's leg due to discomfort and provides optimum offloading for extended periods of time.

Figure 3:
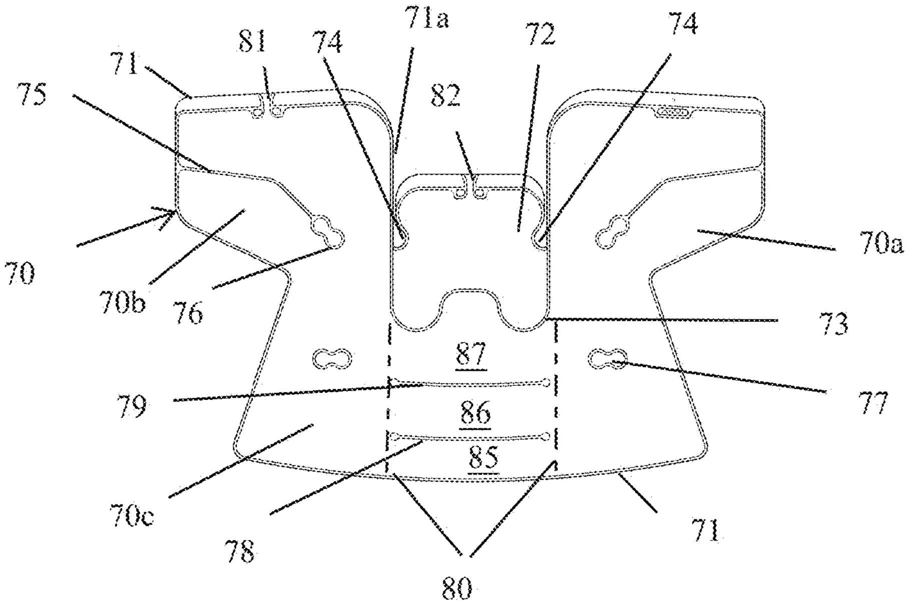
FIG. 3 is a plan view of a static air bladder removably positioned within the therapeutic cushioning boot shown in FIG. 1.

Details of the static air bladder 70 are shown in FIG. 3. The bladder is sealed around its perimeter at a welded seam 71. The contour of the perimeter or seam generally conforms to the contour of the first and second sidewall panels 30, 31 up to the fold seams 26*a, b*, and the rear panel 33, since the bladder is configured to be placed within the pocket 36 defined by the outer and inner panels 11, 12, as described above. Thus, the bladder includes a first region 70*a* that is seated within the pocket at the first sidewall panel 30, a second region 70*b* that is seated within the pocket at the second sidewall panel 30, and a third region 70*c* that is seated within the rear panel 33. The three regions 70*a*-70*c* are in communication with each other and are commonly inflated. The perimeter/seam 71 defines a notch region 71*a* that generally conforms to the notch 34 in the outer and inner panels between the two sidewall panels 30, 31. The static air bladder 70 includes an Achilles bladder 72 that extends from the notch region 71*a* to an interior seam 73 that defines the Achilles bladder and isolates that bladder from the main regions 70*a*-70*c* of the static air bladder. The Achilles bladder 72 ensures that the region of the boot is in direct contact with the patient's Achilles tendon to reduce the strain on the tendon and the adjacent malleoli.

Figure 5:
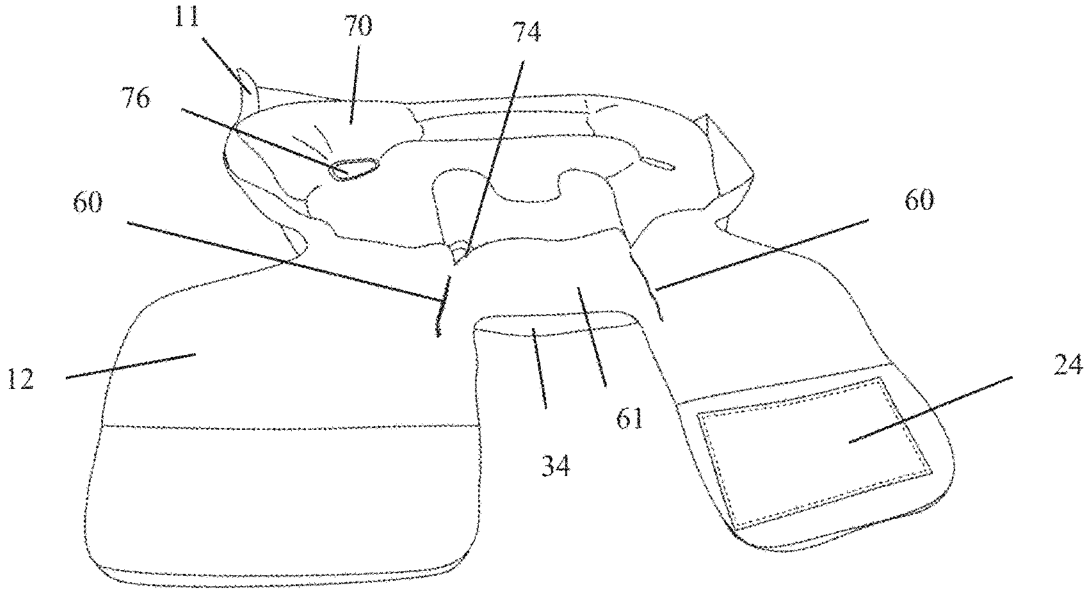
FIG. 5 is a partial cut-away plan view of the cushioning boot showing the position of the air bladder within the cushioning boot.
Figure 6:
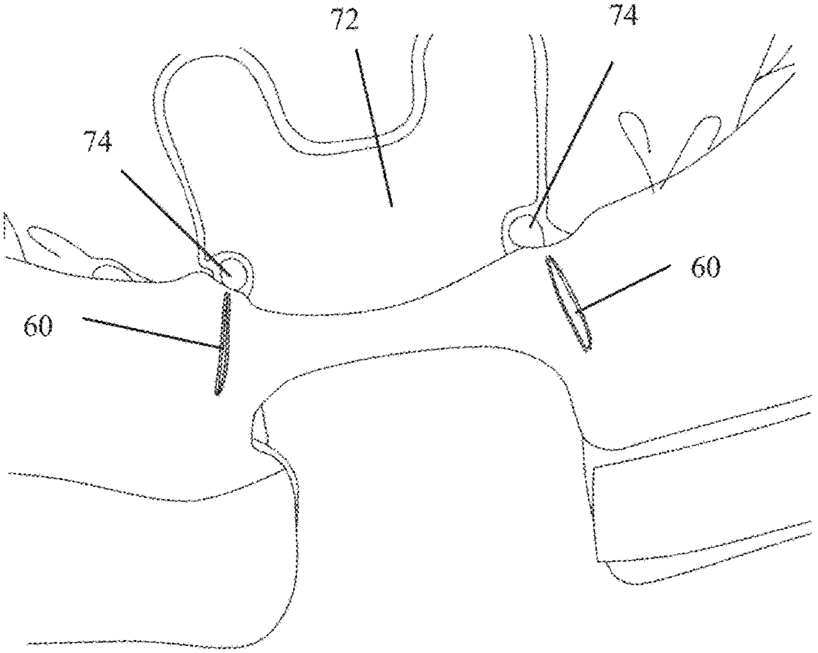
FIG. 6 is an enlarged view from FIG. 5 showing a pair of tubing ports defined in the cushioning boot that cooperate with openings in the air bladder.

In one feature of the therapeutic cushioning boot 10, the bladder is provided with a notch 74 on opposite sides of the Achilles bladder 72. As shown in the detailed view of FIG. 6, these notches 74 line up with tubing ports 60 formed in the cushioning boot (see FIGS. 1, 2, 5). The tubing ports are provided to receive medical tubing used in connection with various therapies for promoting wound healing, improved circulation or reduction of swelling. The tubing passes through either or both ports 60 to mate with a therapeutic device seated within the boot, such as an intermittent compression device or a negative pressure wound therapy device. The outer and inner panels 11, 12 of the boot are sewn together at the ports to form, in essence, a sub-pocket 61 that is configured to receive a portion of the Achilles bladder 72 that extends from the notch region 71*a* to the notches 74. When the air bladder 70 is introduced into the pocket 36, the Achilles bladder 72 is guided into the sub-pocket 61, with the notches 74 surrounding the tubing ports 60, as depicted in FIGS. 5-6. The interface between the notches 74 and the tubing ports 60 help lock the static air bladder 70 in position within the pocket 36, reducing the chance of the bladder shifting or bunching within the boot. It can be appreciated that the inflated bladder exerts pressure on the tubing ports to lock the bladder in position.

Returning to FIG. 3, the static air bladder includes a seam 75 extending from the perimeter seam 71 to an interior dog-bone seam 76 in the first and second regions 70*a*, 70*b*. The seams 75, 76 control the inflation of the bladder in the two regions so that the first and second sidewall panels 30, 31 do not balloon outward. The seams thus help maintain a generally uniform thickness of the boot at the foot of the patient, and therefore a generally uniform pressure to comfortably hold the foot upright relative to the lower leg.

The bladder 70 and the Achilles bladder 72 are each provided with respective inflation ports 81, 82. However, it is contemplated that the ports are sealed after the bladders have been filled to facilitate passage of the bladder through the pocket opening 36*a*, placement of the bladder within the pocket 36, and engagement of the notches 74 around the tubing ports 60. In one embodiment, the bladder 70 is inflated to a pressure that allows immersion and protection of the malleoli when the patient is laying on a side and the back of the lower leg is in the supine position. The Achilles bladder 72 is inflated to a pressure ensuring proper off-loading of the heel when the patient is in the supine position.

Figure 7:
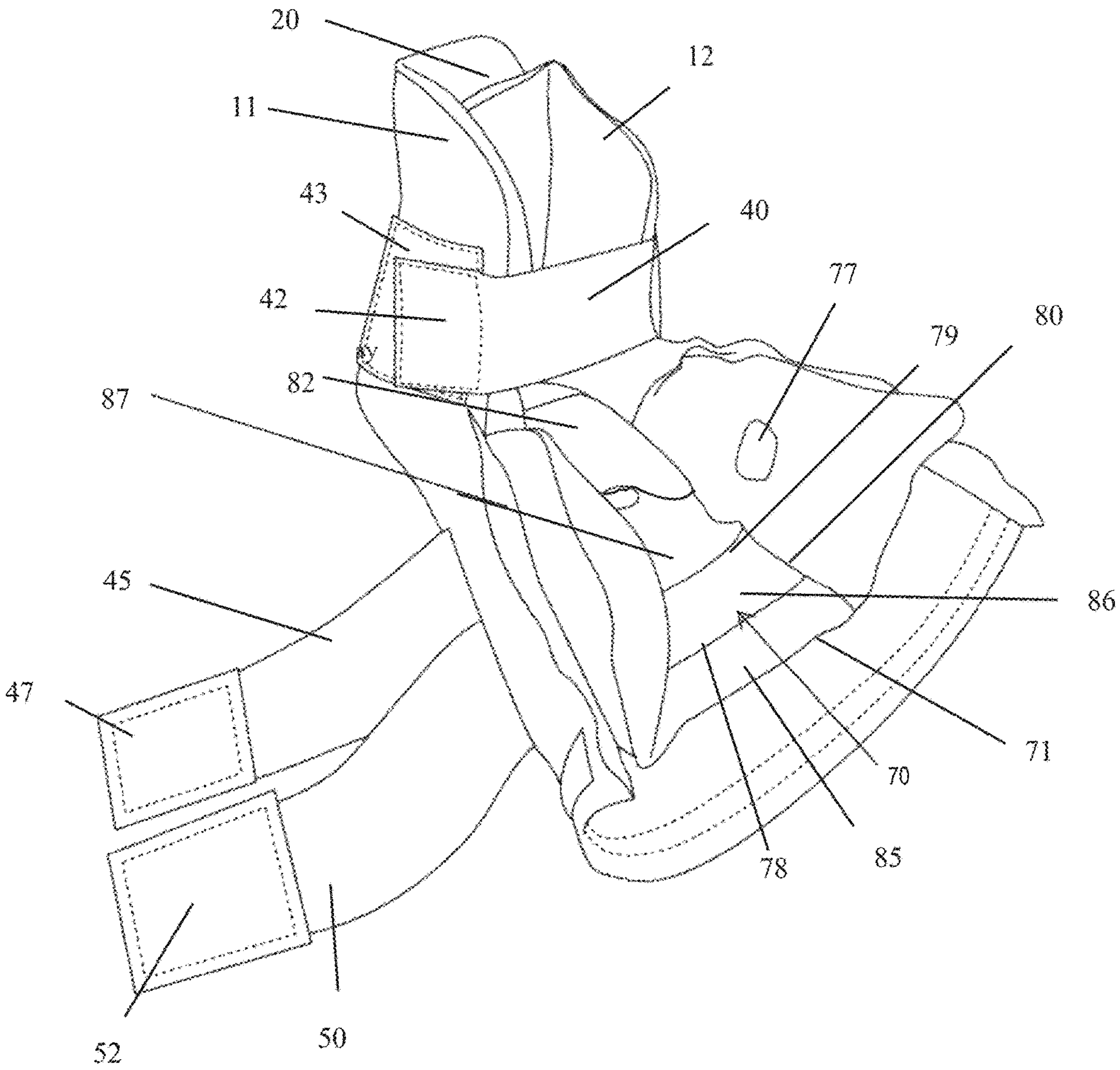
FIG. 7 is a top perspective partial cut-away view of the cushioning boot of FIG. 1 shown in its assembled configuration showing the position of the air bladder within the boot.
Figure 8:
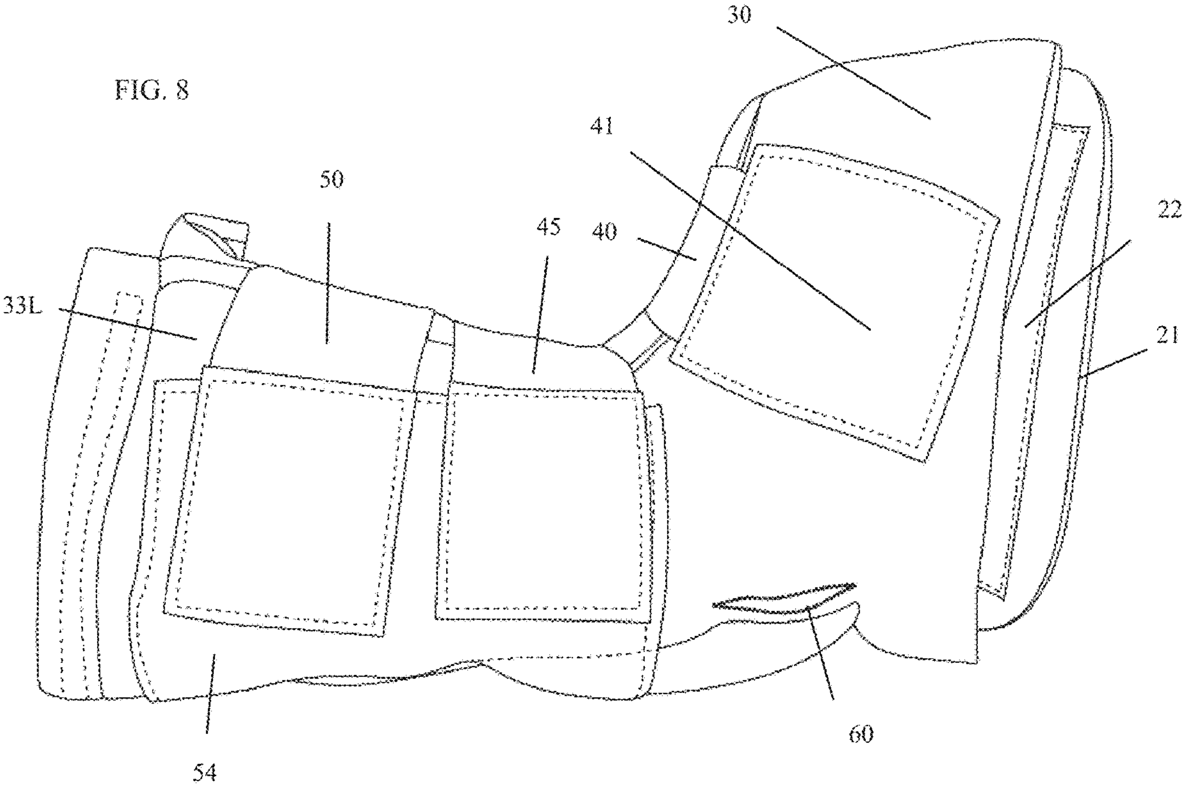
FIG. 8 is a side view of one side of the assembled therapeutic cushioning boot according to the present disclosure.
Figure 10:
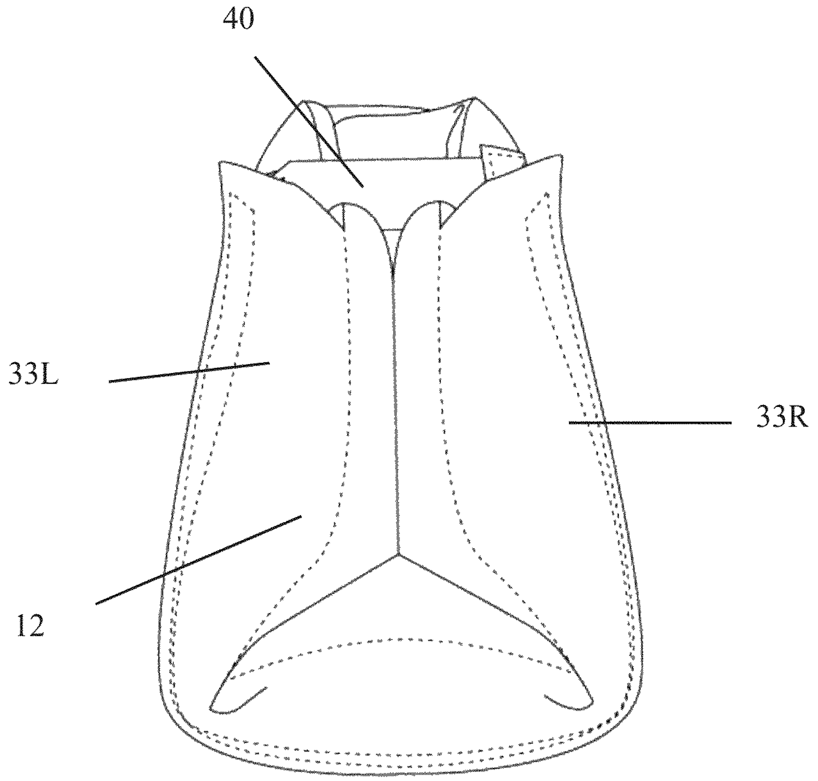
FIG. 10 is a top view of the assembled therapeutic cushioning boot shown in FIG. 8.
Figure 11:
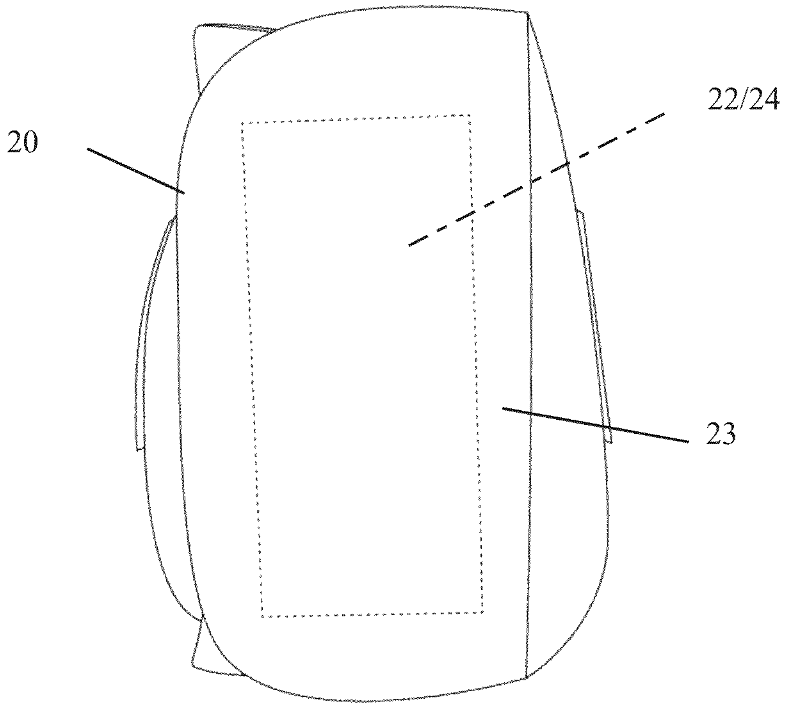
FIG. 11 is a bottom view of the assembled therapeutic cushioning boot shown in FIG. 8.

In another feature, the static air bladder 70 includes a pair of seam lines 78, 79 in the third region 70*c* of the bladder that aligns with the rear panel 33 of the boot. The seam lines 78, 79 extend transversely, and generally parallel to the transverse extent of the opening 36*a*, across the middle third of the bladder so that the seams end at the portions of the rear panel 33 that are bent upward to flank the patient's lower leg, as shown in FIGS. 7 and 10. As shown in FIG. 7 (in which the inner panel 12 removed to show the bladder 70 in its position within the pocket 36), the seams 78, 79 extend between the fold lines 80 (shown in phantom in FIG. 3) so that the seams do not interfere with the ability to wrap the rear panel 33 around the patient's lower leg. The seam 78 is formed at a certain distance from the perimeter seam 71, the seam 79 is formed at a longer distance from the seam 78 and the distance from the seam 79 to the Achilles bladder 82 is greater still. These distances are configured so that the height of the air bladder in the center of the read panel 33 gradually increases from the top of the boot to the foot portion of the boot. Thus, the first segment 85 that is adjacent to the outer perimeter 71 of the bladder has a lower height than the second segment 86, which has a lower inflated height than the third segment 87. The Achilles bladder 82 can be configured to have a greater height than the third segment 87. This ramp-up in height corresponds to the general anatomy of the lower leg from the calf to the ankle. The increasing distance between successive seams provides more length of the bladder to be inflated, thereby permitting a successive increase in bladder height. This feature reduces localized high pressure by distributing the pressure more evenly across the bladder at the leg region. This feature also ensures that the Achilles tendon and heel are cradled by the boot, thereby improving overall comfort and pressure off-loading. In one specific embodiment, the seams 78, 79 are positioned for a ramp angle of 16-20 degrees, and preferably at 18.5 degrees.

Returning to FIGS. 1-2, the therapeutic cushioning boot 10 includes an array of straps that are used to hold the patient's lower leg and foot within the boot. Thus, the boot includes a foot strap 40 that is fastened to the first sidewall panel 30 at anchor 41 and that includes a hook-and-loop fastener pad 42 at the free end of the strap. The anchor 41 can be formed by stitching the foot strap to the outer panel 11. The anchor 41 can optionally include a hook-and-loop fastener surface. The fastener pad 42 of the foot strap is arranged to engage an attachment pad 43 affixed to the outer panel 11 at the second sidewall panel 31. The foot strap 40 and attachment pad 43 are oriented so that the foot strap spans the space between the first and second sidewall panels 30, 31 when the cushioning boot 10 is folded as shown in FIGS. 7, 12-14 to embrace the foot of the patient. The fastener pad 42 and attachment pad 43 are sized to allow variation in the space between the sidewall panels to accommodate different widths of patients' feet. The foot strap 40 can also be formed of an elastic material to maintain a certain tightness of the sidewall panels on the foot of the patient to effectively hold the foot in the desired upright position.

Figure 12:
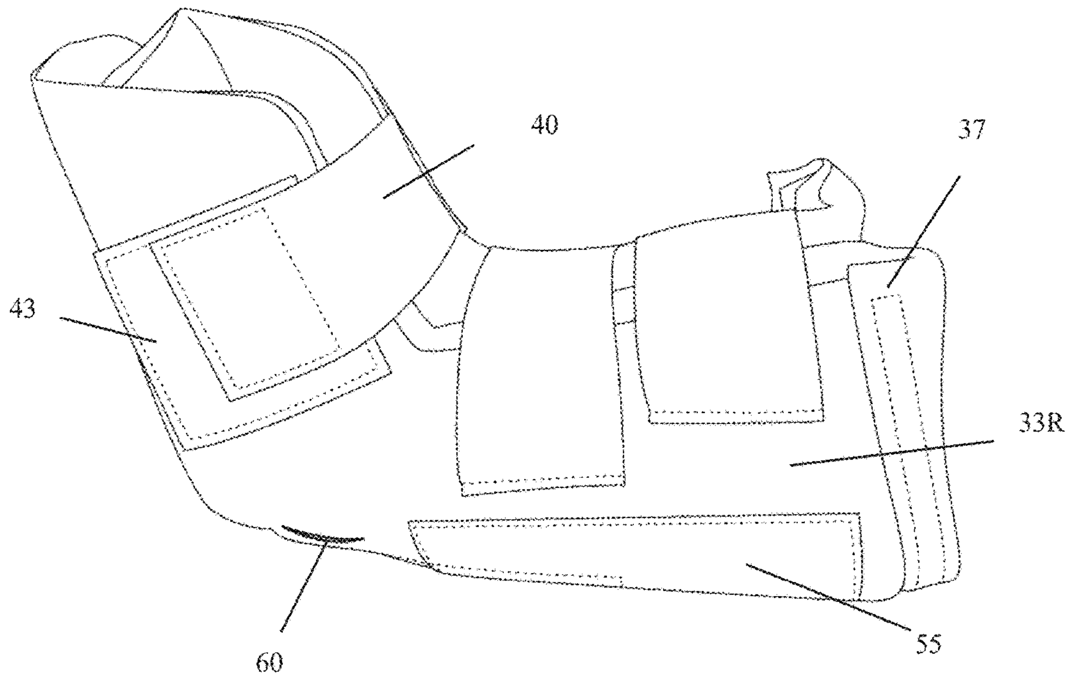
FIG. 12 is a side perspective view of the assembled therapeutic cushioning boot shown in FIG. 8.

The boot 10 further includes a lower leg strap 45 and an upper leg strap 50 attached to one side of the rear panel 33 at respective anchors 46, 51. As with the foot strap, the anchors 46, 51 can be stitched to the outer panel 11. The lower leg strap 45 is positioned closest to the sidewall panels 30, 31 so that when the boot 10 is folded as shown in FIGS. 7, 12 the strap extends across the space directly above the patient's ankle. The upper leg strap 50 is offset from the lower leg strap so that the strap extends across the lower end of the patient's calf. The two straps 45, 50 include corresponding inner hook-and-loop fastener pads 47, 52 at the free end of the straps. The pads 47, 52 are provided on the inward facing surface of the straps when the straps are extended across the folded boot, as shown in FIG. 2. The pads 47, 52 are arranged to engage an attachment pad 54 fastened to the opposite side of the rear panel 33, as shown in FIG. 1. Again, the attachment pad 54 can be stitched to the outer panel 11 of the boot. The fastener pads 47, 52 and attachment pad 54 are sized to permit some variability in the space between the opposite sides of the rear panel when it is folded about the patient's lower leg, to account for different sizes of patient's legs. As with the foot strap, the two leg straps can be formed of an elastic material.

In one feature of the boot 10, the two leg straps 45, 50 are positioned on the opposite side of the body portion 15 from the foot strap 40. In other words, the foot strap 40 is anchored to the first sidewall panel 30 just above the left side 33L of the rear panel 33. The two leg straps are anchored to the right side 33R of the back panel 33. The foot strap is attached to the attachment pad 43 on the second sidewall panel 31 just above the right side 33R of the rear panel, and the two leg straps 45, 50 are attached to the attachment pad 54 on the left side 33L of the rear panel. This alternating strap orientation prevents unintended misalignment of the therapeutic boot 10 that can result from attaching the foot strap to the attachment pad for the leg straps, or vice versa. The alternating strap orientation also ensures a secure fit of the boot on the patient's foot and lower leg, regardless of the movement of the patient.

Figure 9:
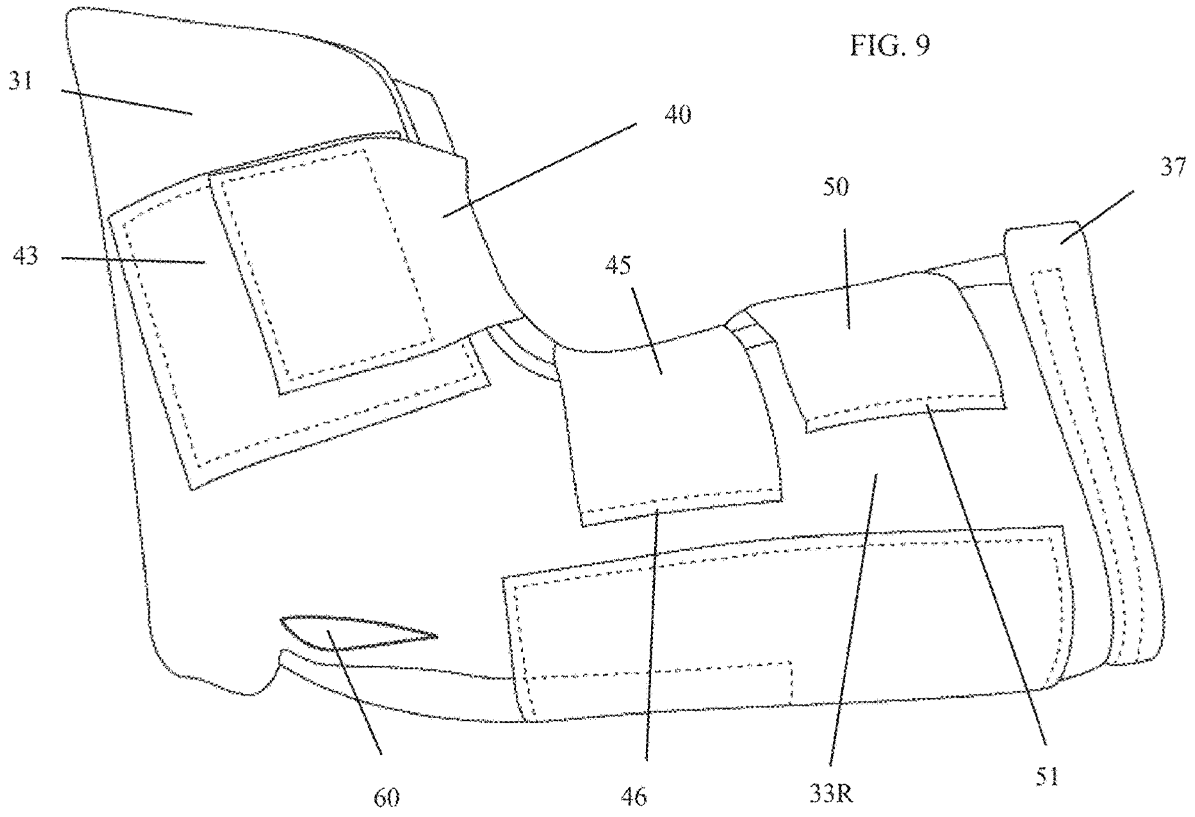
FIG. 9 is a side view of the opposite side of the assembled therapeutic cushioning boot shown in FIG. 8.

In another feature of the boot 10, the anchors of the two leg straps 45, 50 are offset, as shown in FIGS. 1 and 9. In particular, the anchor 46 of the lower leg strap 45 is positioned inboard of the anchor 51 of the upper leg strap 50. The lower leg strap 45 thus overlaps more of the right side 33R of the back panel 33 when the boot is closed (as in FIG. 9) than the upper leg strap 50. Likewise, the upper leg strap 50 overlaps more of the left side 33L of the back panel 33 when the boot is closed (as in FIG. 8) than the lower leg strap 45. In the preferred embodiment, the two straps are the same length.

Figure 15:
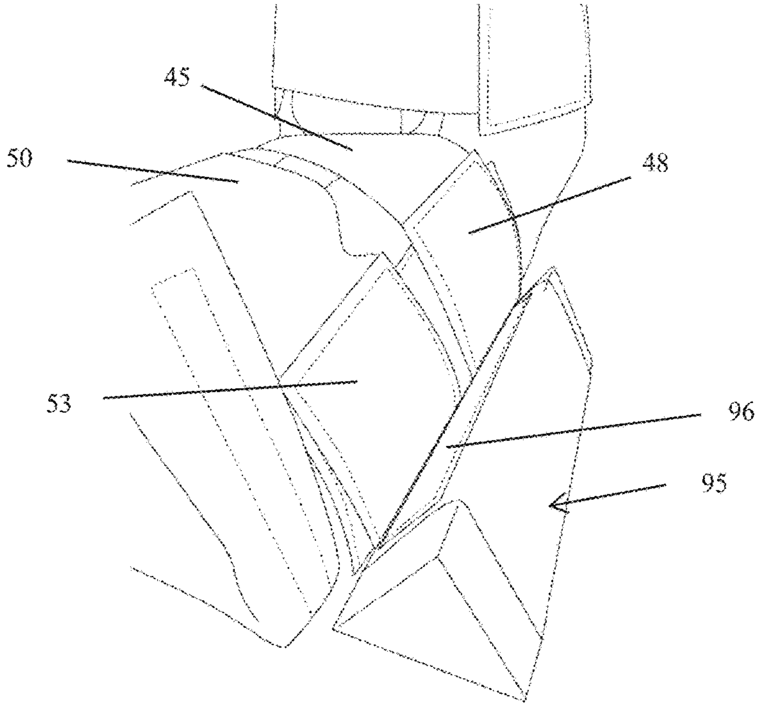
FIG. 15 is a top perspective view of the assembled therapeutic cushioning boot shown in FIG. 8, depicted with a positioning wedge.

The therapeutic cushioning boot 10 can be used with a support wedge 95, as shown in FIG. 15. The support wedge 95 is an elongated generally triangular body that helps maintain the boot 10 in a proper orientation, namely with the foot pointing upward away from the bed. The wedge 95 includes a fastening surface 96 that can comprise a hook-and-loop fastener. The outside faces of the attachment ends of the leg straps 45, 50 are provided with a mating fastener pad 48, 53, respectively, to which the fastening surface 96 can attach on the left side 33L of the boot. The opposite side 33R of the body 15 can be provided with an attachment pad 55 (FIG. 1) to which the support wedge 95 can also be attached. The outer fastening pads 48, 53 on the leg straps and the secondary attachment pad 55 are positioned so that the support wedge can be attached to the cushioning boot 10 with the boot in an optimum position for supporting the lower leg and foot of the patient.

In use, the boot 10 is initially provided in its open configuration, as shown in FIGS. 1-2. The filled static air bladder 70 is introduced into the opening 36*a* of the pocket and then pushed into the pocket until the two notches 74 engage the tubing ports 60 situated on either side of the notch 34 in the boot body 15. The end of the Achilles bladder 72 contacts the outer seam 13 of the body 15 and the main regions 70*a*, 70*b* are positioned within the first and second sidewall panels 30, 31, respectively. The closure 37 is folded over the opening with the fastener strips 38, 39 engaged to close the bladder within the pocket 36. If an additional therapeutic device, such as a wound therapy device, is provided, the device is placed in an appropriate position on the open boot 10 and the associated tubing is fed through the tubing ports 60.

The boot 10 is then laid out on the bed and the patient's leg is placed on the open boot so that the patient's heel is within the notch 34 and the Achilles tendon is resting on the portion of the boot with the Achilles bladder 72. The two sidewall panels 30, 31 are folded about the patient's foot and, with the foot sitting vertically, the first overlapping panel 21 is folded inward against the bottom of the patient's foot. The second overlapping panel 23 is folded inward over the first panel so that the first and second hook-and-loop fasteners 22, 24 engage to close the foot gate 20 of the boot. The foot strap 40 can be drawn across the foot gate and attached to the attachment pad 43 to hold the patient's foot in position. The left and right sides 33L, 33R of the rear panel 33 are fully folded against the sides of the patient's lower leg and the two leg straps 45, 50 are drawn across the patient's leg to engage the main attachment pad 54. The caregiver can then readily orient the patient's leg and introduce the support wedge 95 on either side, or both sides, of the boot 10, to support the boot so that the patient does not have to worry about holding the lower leg stable.

The present disclosure should be considered as illustrative and not restrictive in character. It is understood that only certain embodiments have been presented and that all changes, modifications and further applications that come within the spirit of the disclosure are desired to be protected

What is claimed is:

1. A therapeutic compression boot, comprising:

an outer panel and an inner panel, each having a common outer perimeter that defines, in a planar open configuration of the therapeutic compression boot, a back panel, a first sidewall panel and a second sidewall panel, each sidewall panel extending from one end of said back panel parallel to each other and separated from each other by a notch, a foot gate including a first overlapping panel foldably attached to an end of said first sidewall panel, and a second overlapping panel foldably attached to said second sidewall panel, wherein the outer perimeter of the outer panel is connected to the inner panel to define an interior pocket therebetween with an opening at an opposite end of said back panel, wherein said inner panel includes a closure extending beyond said outer panel at said opposite end of said back panel, said closure configured to be folded over said opening, said closure and said outer panel including mating fastener strips for releasably fastening said closure to said outer panel, and wherein at least said inner panel contains a cushioning material in at least a portion of said back panel and in said first and second overlapping panels of said foot gate;

a static air bladder sized to be removably received through said opening and within said interior pocket, said static air bladder including a sealed outer perimeter defining a first region conforming to and receivable within said first sidewall panel, a second region conforming to and receivable within said second sidewall panel and a third region conforming to and receivable within said back panel said first, second, and third regions are commonly inflated; and a plurality of straps, each anchored at a first side of said outer panel and including a fastener at a free end thereof, each of said plurality of straps having a length sized to extend across said therapeutic compression boot in a folded condition to engage an attachment pad on a second side of said outer panel to hold the therapeutic compression boot in said folded condition.

2. The therapeutic compression boot of claim 1, wherein said static air bladder includes an Achilles bladder separate from said first, second, and third regions, said Achilles bladder disposed between and connected to said first and second regions adjacent said notch.

3. The therapeutic compression boot of claim 2, wherein:

said third region of said static air bladder has a transverse extent parallel to said opening and includes a pair of parallel seams extending across a middle one-third of said transverse extent of the static air bladder, a first one of said parallel seams offset from said sealed perimeter of said static air bladder by a first dimension, a second one of said parallel seams offset from said first one of said seams by a second dimension, and the second one of said parallel seams offset from said Achilles bladder by a third dimension, said static air bladder includes a first inflated segment between said sealed perimeter and said first one of said parallel seams, a second inflated segment between said first and second one of said parallel seams, and a third inflated segment between said second one of said parallel seams and said Achilles bladder, and said third dimension is greater than said second dimension, which is greater than said first dimension so that said third inflated segment is inflated to a greater height than said second inflated segment, which is inflated to a greater height than said first inflated segment.

4. The therapeutic compression boot of claim 3, wherein the heights of said first, second, and third inflated segments form a ramp from said sealed perimeter to said Achilles bladder, and wherein said first, second, and third dimensions are configured to produce a ramp angle of 16-20 degrees.

5. The therapeutic compression boot of claim 3, wherein said Achilles bladder is inflated to a greater height than said third inflated segment of the third region of said static air bladder.

6. The therapeutic compression boot of claim 2, wherein said Achilles bladder includes an inflation port and said static air bladder includes an inflation port in one of said first and second regions separate from the inflation port of said Achilles bladder.

7. The therapeutic compression boot of claim 2, wherein: said outer and inner panels each define a tubing port in each of said first and second sidewall panels configured for passage of a tubing therethrough, said outer and inner panels are connected at each tubing port; and said Achilles bladder is connected to said first and second regions of said static air bladder to define a pair of notches aligned with and configured to engage each tubing port to retain said static air bladder within the interior pocket.

8. The therapeutic compression boot of claim 1, wherein said outer panel is formed of a first pair of sheets sewn together at said outer perimeter to encase said cushioning material, said inner panel is formed of a second pair of sheets sewn together at said outer perimeter to encase said cushioning material, and a material of the first pair of sheets is different from a material of the second pair of sheets.

9. The therapeutic compression boot of claim 8, wherein the material of said second pair of sheets is softer than the material of said first pair of sheets.

10. The therapeutic compression boot of claim 9, wherein the material of said second pair of sheets is microsuede and the material of said first pair of sheets is non-woven nylon.

* * * * *